(12) United States Patent
Whitaker et al.

(10) Patent No.: US 8,911,378 B2
(45) Date of Patent: Dec. 16, 2014

(54) CUFF INTEGRITY DETECTION DURING INFLATION OF AN AUTOMATED BLOOD PRESSURE DEVICE

(75) Inventors: Tyson B. Whitaker, Arden, NC (US); Matthew J. Kinsley, Liverpool, NY (US); Joseph D. Buchanan, Waynesville, NC (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 544 days.

(21) Appl. No.: 13/052,279

(22) Filed: Mar. 21, 2011

(65) Prior Publication Data

US 2012/0245478 A1 Sep. 27, 2012

(51) Int. Cl.
*A61B 5/02* (2006.01)
*A61B 5/022* (2006.01)
*A61B 5/00* (2006.01)

(52) U.S. Cl.
CPC ......... *A61B 5/022* (2013.01); *A61B 2560/0475* (2013.01); *A61B 5/7203* (2013.01)
USPC ............................ 600/499; 600/485; 600/490

(58) Field of Classification Search
CPC .... A61B 5/022; A61B 5/021; A61B 5/02208; A61B 5/02225; A61B 5/024; A61B 5/02233
USPC .................. 600/490–496, 499–503
See application file for complete search history.

(56) References Cited

U.S. PATENT DOCUMENTS

| | | | |
|---|---|---|---|
| 3,348,534 A * | 10/1967 | Marx et al. ................... | 600/492 |
| 3,905,353 A | 9/1975 | Lichowsky et al. | |
| 4,295,471 A * | 10/1981 | Kaspari ........................ | 600/488 |
| 4,493,326 A | 1/1985 | Hill et al. | |
| 2009/0156946 A1 | 6/2009 | Lane et al. | |
| 2010/0030302 A1* | 2/2010 | Blowers et al. ................ | 607/60 |
| 2011/0009756 A1* | 1/2011 | Merilainen .................. | 600/490 |
| 2011/0105927 A1* | 5/2011 | Greenhut et al. ............. | 600/513 |

FOREIGN PATENT DOCUMENTS

JP 2060633 C 3/1990

OTHER PUBLICATIONS

Wolfram Mathworld, definition of statistical range; see cited references with the document that date to 1962, 1968, and 1995.*
International Search Report and Written Opinion in PCT/US2012/029204 mailed Sep. 27, 2012, 8 pages.

* cited by examiner

*Primary Examiner* — Michael Kahelin
*Assistant Examiner* — Tho Tran

(57) ABSTRACT

A method for detecting cuff slippage in a blood pressure monitoring device includes starting a cuff inflation on the blood pressure monitoring device. A plurality of pressure samples is obtained when the cuff is inflating. A level of background noise is determined during the cuff inflation. The level of background noise is determined from the plurality of pressure samples. When the background noise is determined, a determination is made from the plurality of blood pressure readings whether a pressure pattern indicating cuff slippage is obtained.

11 Claims, 14 Drawing Sheets

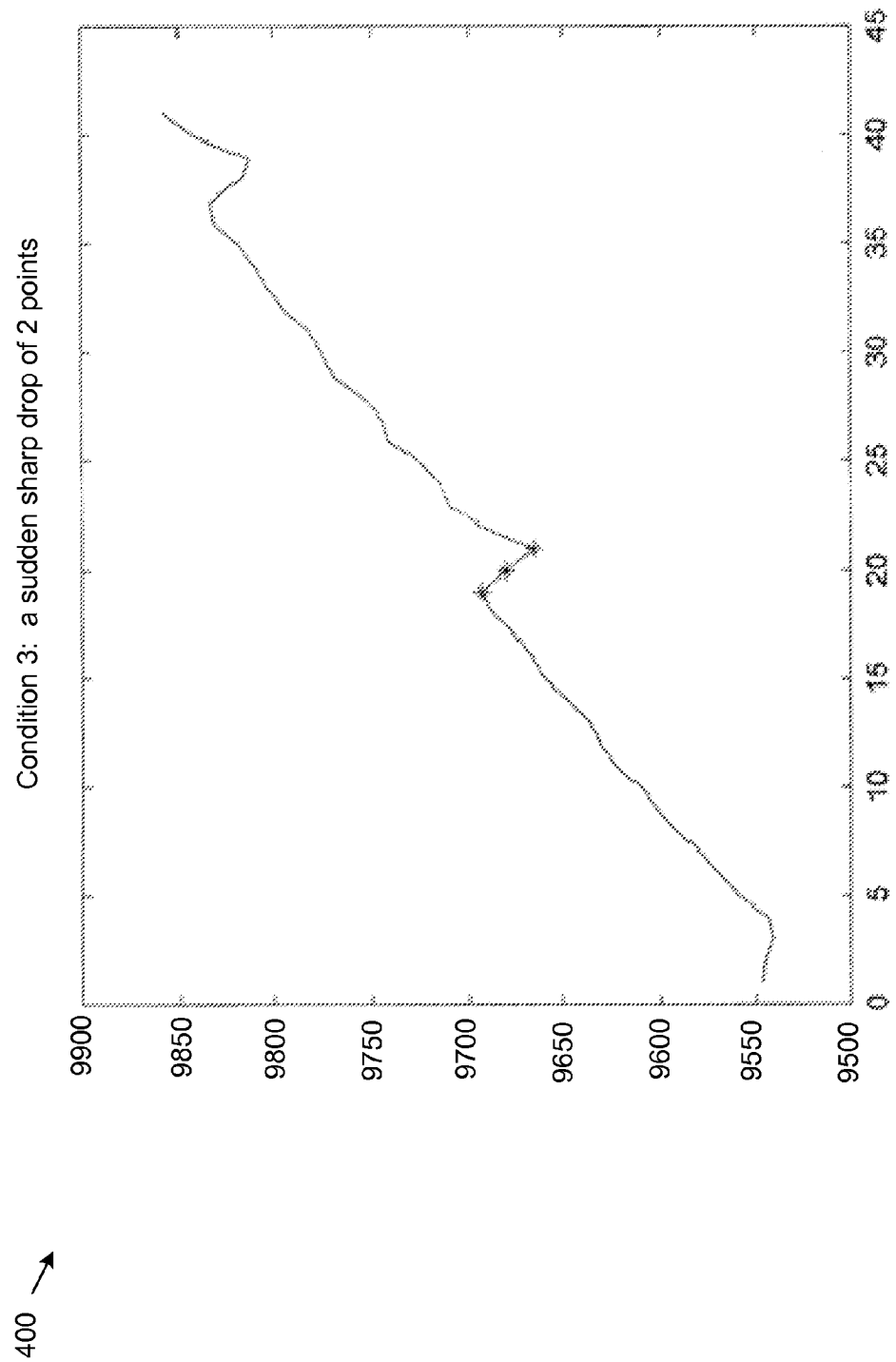

Condition 1:

Slope > 0
AND
P(n-3) > P(n-2) + 1.5 * noise
AND
P(n) > P(n-1) + 1.5 * noise

FIG. 5A

Condition 2:

Slope > 0
AND
P(n-4) > P(n-3) + 1.5 * noise
AND
P(n) > P(n-1) + 1.5 * noise
AND
P(n-2) < P(n-3)
AND
P(n-2) < P(n-1)

FIG. 5B

Condition 3:

Slope > 0
AND
P(n-2) > P(n-1) + 2.25 * noise
AND
P(n-1) > P(n) + 2.25 * noise

FIG. 5C

CUFF INTEGRITY DETECTION DURING INFLATION OF AN AUTOMATED BLOOD PRESSURE DEVICE

BACKGROUND

Automated blood pressure machines provide an easy and convenient means for medical professionals to monitor the blood pressure of their patients. The ease of use of these machines also makes them common in the home, where people can monitor their own blood pressure free of the stress of a medical setting.

One of the key elements of an automated blood pressure machine is the blood pressure cuff. The cuff must be secure around the patient's arm and provide minimal slippage during cuff inflation. Blood pressure cuffs commonly include a material such as Velcro to enable ease of fastening and removal of the cuff and to provide secure fastening of the cuff.

Blood pressure cuffs, particularly those used for automated blood pressure machines in physicians' offices, are typically used for a large number of cycles and for many years. Velcro tends to wear out and, when it does wear out, the cuff tends to slip during inflation, sometimes causing inaccurate blood pressure readings or causing errors that prevent the blood pressure machine from determining a patient's blood pressure. However, it is not always clear to the physician or patient that inaccurate or incomplete blood pressure readings are caused by cuff slippage.

SUMMARY

Embodiments of the disclosure are directed to systems and methods for detecting cuff slippage in a blood pressure monitoring device. In one aspect, a cuff inflation is started on the blood pressure monitoring device. The cuff inflation includes a blood pressure cuff. A plurality of pressure samples is obtained when the cuff is inflating. A determination is made whether a slope corresponding to the plurality of pressure samples is a positive number. When it is determined that the slope is a positive number, a level of background noise during the cuff inflation is determined. The level of background noise is determined from the plurality of pressure samples. When the background noise is determined, a determination is made from the plurality of pressure samples whether a pressure pattern indicating cuff slippage is obtained.

The details of one or more techniques are set forth in the accompanying drawings and the description below. Other features, objects, and advantages of these techniques will be apparent from the description, drawings, and claims.

DESCRIPTION OF THE DRAWINGS

FIG. 4 shows an example pattern of pressure samples that signifies a third cuff slippage condition.

FIGS. 5A, 5B and 5C show example mathematical formulas used to evaluate the slippage conditions of FIGS. 2, 3 and 4.

DETAILED DESCRIPTION

Figure 1:
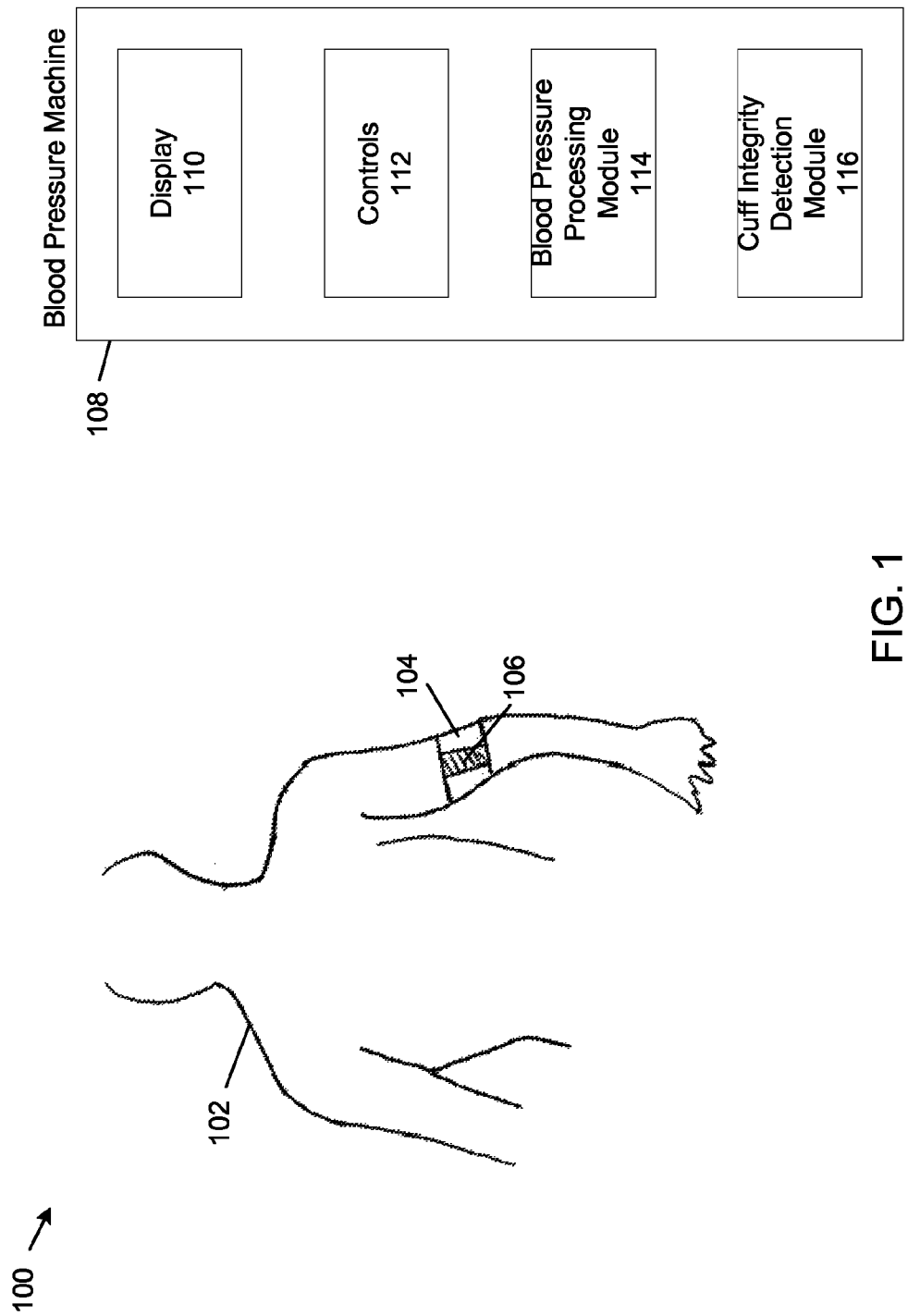
FIG. 1 shows an example system that includes an automatic blood pressure machine.

The present disclosure is directed to systems and methods for determining when cuff slippage occurs during a blood pressure measurement on an automated blood pressure machine. When a cuff slippage condition occurs, the blood pressure machine takes an appropriate action, such activating an alert or terminating the blood pressure measurement. If the slippage condition is not severe, the blood pressure machine may ignore the slippage condition and continue with the blood pressure measurement.

Blood pressure is typically measured by two numbers—a systolic blood pressure and a diastolic blood pressure. The systolic blood pressure corresponds to a blood pressure when the heart is contracting, corresponding to the maximum arterial pressure during contraction of the left ventricle of the heart. The diastolic blood pressure corresponds to a blood pressure when the heart is relaxing, corresponding to the minimum arterial pressure during relaxation. During each heartbeat, blood pressure varies between a maximum (systolic) value and a minimum (diastolic) value. A person's blood pressure is commonly expressed in terms of the systolic blood pressure over the diastolic blood pressure, in units of millimeters (mm) of Mercury (Hg), for example 120/80 mmHg.

A blood pressure measurement comprises an inflation cycle in which the cuff is inflated, followed by a deflation cycle during in which the cuff is deflated. Typically, the blood pressure machine inflates the cuff to an appropriate pressure above the systolic pressure. The blood pressure machine then starts a deflation cycle during which systolic pressure and the diastolic pressure are measured.

Cuff slippage, when it occurs, typically occurs during the inflation cycle when the cuff is expanding. Because the cuff must be securely fastened to the arm of a patient in order to obtain an accurate blood pressure reading, any slippage condition may result in an inaccurate reading, or if the slippage condition is severe, the slippage condition may prevent the blood pressure machine from completing a blood pressure measurement.

A blood pressure cuff is typically made from a fabric that than be wrapped around the arm of a patient. The cuff typically includes a fastening material, such as Velcro, that can be used to secure the cuff to the patient and also permit the patient to easily remove the cuff. Velcro is a fastener that typically consists of two strips of fabric—one strip having a plurality of tiny hooks and the other having a plurality of tiny loops. When the strip having the plurality of tiny hooks is placed against the strip with the plurality of tiny loops, the hooks grab onto the loops and fastening occurs. One of the strips can be pulled away from the other to separate the strips. In this disclosure, the terms fastening material and Velcro are used interchangeably.

Velcro may be made from a variety of fabrics, such as cotton, Nylon and polyester. Velcro may also be made from plastic or other materials. However, when Velcro ages, it is common for the hooks and loops to wear out so that the fastening action of the Velcro may tend to weaken. When used on a blood pressure cuff, this weakening may cause cuff slippage, particularly during the inflation cycle.

When a cuff slippage condition is detected, an appropriate form of action may be taken. The form of the action is dependent on the severity of the slippage condition. If the slippage condition is such that a blood pressure for the patient cannot be calculated, the automated blood pressure machine terminates the blood pressure measuring operation. Typically the blood pressure measuring operation is terminated by deflating the cuff. In addition, an alert may be provided for the patient or physician, indicating that the blood pressure measuring operation has been terminated. The alert may take one of several forms, such as an audible alert and a display message on the automatic blood pressure machine. When the slippage condition is not severe enough to interfere with the blood pressure measurement, the automated blood pressure machine may ignore the slippage condition and continue the cuff inflation.

FIG. 1 shows an example system 100 from which a blood pressure reading can be made. The example system 100 includes an example patient 102 and an example automated blood pressure machine 108. An example blood pressure cuff 104 is fastened around the left arm of the patient. The blood pressure cuff 104 includes an example fastening material 106, typically Velcro.

The example automated blood pressure machine 108 includes a display 110, controls 112, a blood pressure processing module 114 and a cuff integrity detection module 116. The example display 110 displays a read out of the blood pressure during cuff inflation and deflation. At the completion of the blood pressure measurement, the blood pressure is displayed, typically as the systolic pressure over the diastolic pressure. In addition, other physiological data may be displayed, for example the patient's heart rate. The example controls 112 may include an on/off button, a start button or other similar controls.

A tube (not shown in FIG. 1) connects the blood pressure cuff 104 to the automatic blood pressure processing machine 108. During cuff inflation, the tube supplies air to the blood pressure cuff 104, causing the blood pressure cuff 104 to inflate, tightening around the arm of the patient. As the blood pressure cuff 104 tightens around the arm of the patient, the blood flow through the patient's artery is affected.

The example blood pressure processing module 114 uses information received from the blood pressure cuff 104 to calculate the blood pressure of the patient. When blood flows through the radial artery under the blood pressure cuff, pressure pulses are created. The blood pressure processing module 114 receives pressure pulse information from the blood pressure cuff 104. The blood pressure processing module 114 uses the pressure pulse information in conjunction with an algorithm to calculate the systolic and the diastolic blood pressure of the patient.

The example cuff integrity detection module 116 determines when a cuff slippage condition occurs. Cuff slippage may be detected when various patterns of blood pressure readings occur during a cuff inflation. For example, normally during a cuff inflation the blood pressure readings tend to increase until a maximum value is reached. However, during a slippage condition, decreases in blood pressure usually occur. Certain combinations of decreases in blood pressure during a cuff inflation signify a cuff slippage condition, as explained in more detail herein.

Figure 2:
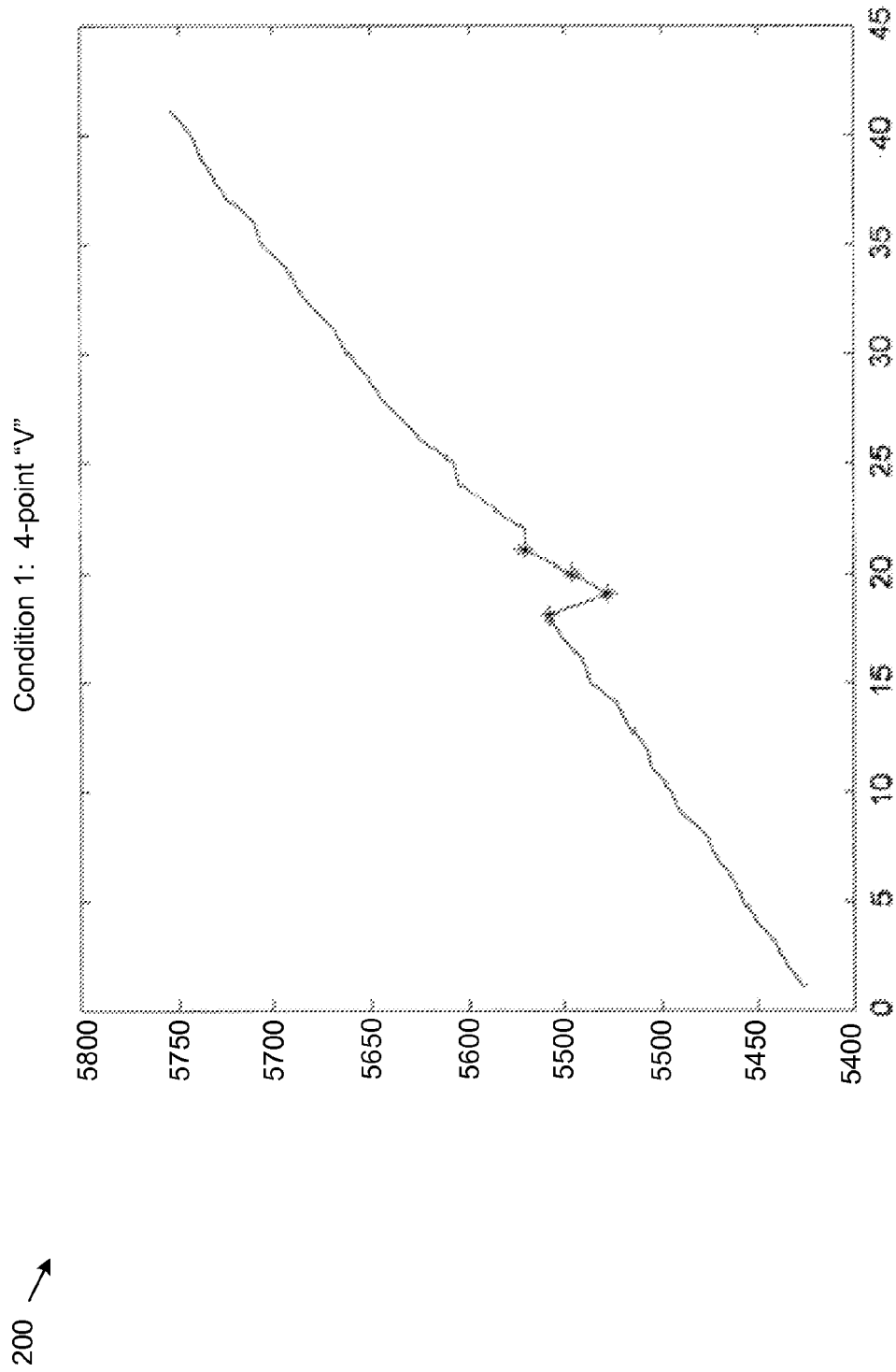
FIG. 2 shows an example pattern of pressure samples that signifies a first cuff slippage condition.

FIG. 2 shows an example pattern 200 of pressure samples during a cuff inflation that signifies one type of cuff slippage condition. The example pattern 200 signifies a slippage condition characterized by a 4-point "V". The horizontal axis of pattern 200 shows numbers corresponding to pressure samples. The vertical axis of pattern 200 shows numbers corresponding to measured pressure in units of 100 mm of Hg. For example, a value of 5600 represents a pressure sample of 56 mmHg.

As shown in FIG. 2, the 4-point "V" corresponds to four specific pressure samples in which the pressure drops and then rises. These four points form a 4-point "V" shape in the example pattern 200. As discussed herein, a specific mathematical formula is evaluated to determine when the slippage condition characterized by the 4-point "V" shape occurs.

Figure 3:
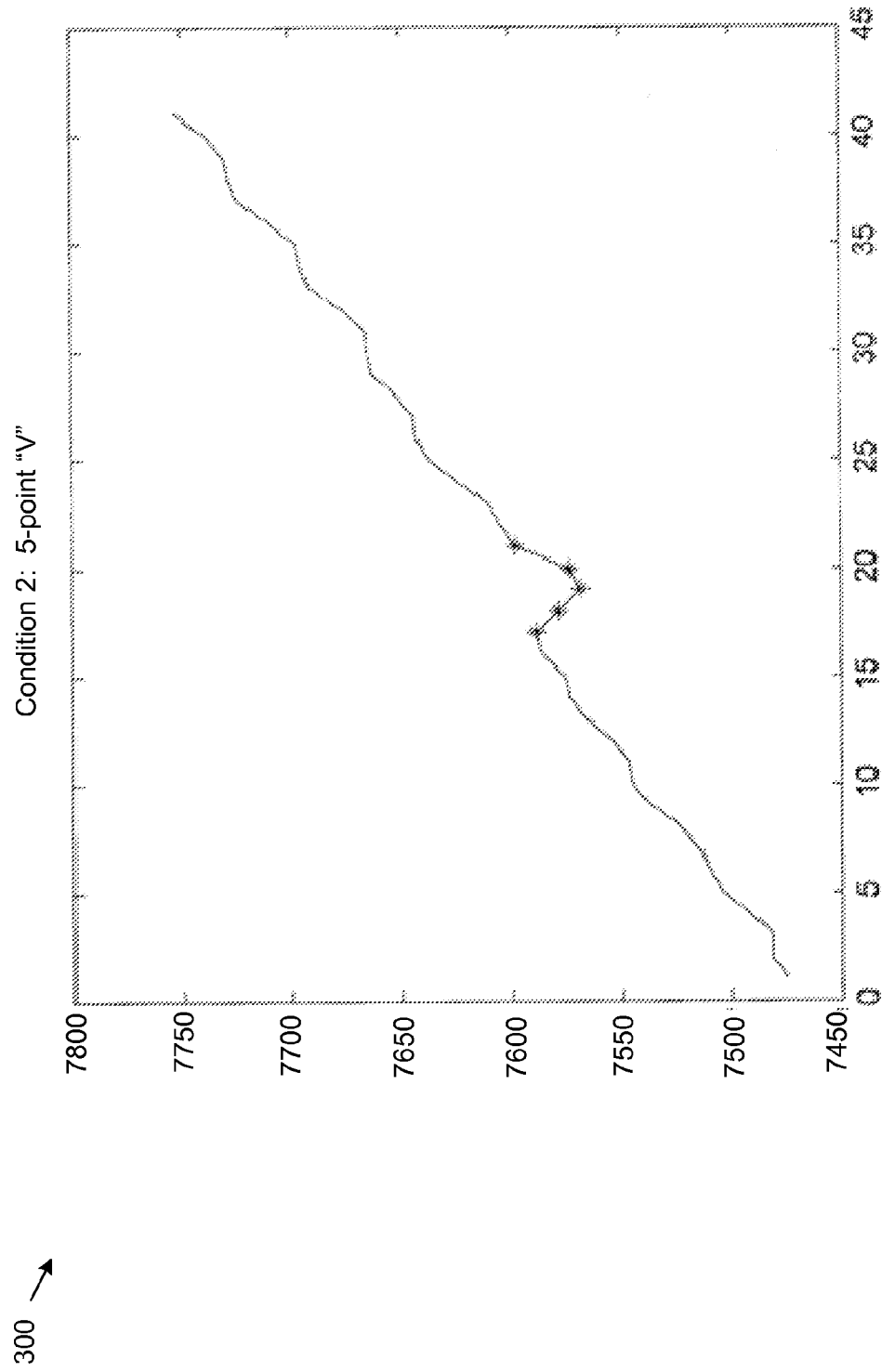
FIG. 3 shows an example pattern of pressure samples that signifies a second cuff slippage condition.

FIG. 3 shows an example pattern 300 of pressure samples during a cuff inflation that signifies a second type of cuff slippage condition. The example pattern 300 signifies a slippage condition characterized by a 5-point "V". The horizontal axis of pattern 300 shows numbers corresponding to pressure samples. The vertical axis of pattern 300 shows numbers corresponding to measured pressure in units of 100 mm of Hg. As shown in FIG. 3, the pressure readings shown on the vertical axis have a range from 7450 to 7800, corresponding to a pressure range of 74.5 mmHg to 78 mmHg. This range is an arbitrary range that is different from the range of 54 mmHg to 58 mmHg shown in FIG. 2. In actual practice, slippage condition 1 and slippage condition 2 can occur at any pressure range that occurs above a minimum level of pressure. The minimum level of pressure is typically 40 mmHg.

As shown in FIG. 3, the 5-point "V" corresponds to five specific pressure samples in which the pressure drops and then rises. These five points form a 5-point "V" shape in the example pattern 300. As discussed herein, a specific mathematical formula is evaluated to determine when the slippage condition characterized by the 5-point "V" shape occurs.

FIG. 4 shows an example pattern 400 of pressure samples during a cuff inflation that signifies a third type of cuff slippage condition. The example pattern 400 signifies a slippage condition characterized by a sharp drop of pressure that occurs for two successive pressure samples. The sharp drop represents a pressure that is more than 2.25 multiplied by the background noise.

The pressure range shown in FIG. 4, corresponding to 95 mmHg to 99 mmHg is arbitrary. Similar to condition 1 and condition 2, slippage condition 3 can occur during any pressure range above a minimum pressure, typically 40 mmHg. As discussed herein, a specific mathematical formula is evaluated to determine when the slippage condition characterized by pattern 400 occurs.

FIGS. 5A-5C show mathematical formulas used to evaluate slippage conditions 1-3. As shown in FIG. 5A, slippage condition 1 occurs when each of three conditions occur. First, a slope of pressure samples during a cuff inflation must be greater than 0. A description of how the slope is determined is provided later herein. Second, a pressure three samples previous to the current sample (designated as $P(n-3)$, where $P(n)$ is a pressure at the current sample) must be greater than the sum of a pressure two samples previous to the current sample and the product of 1.5 multiplied by a noise level. This condition is designated as $P(n-3)>P(n-2)+1.5\times noise$. The noise level is a number corresponding to a background noise during the cuff inflation, as explained further herein. Third, a pressure at the current sample must be greater than the sum of a pressure one sample previous to the current sample and the product of 1.5 multiplied by the background noise. This condition is designated as P(n)>P(n-1)+1.5×noise. When all three of these conditions are met and when all samples used are greater than a minimum sample, typically 40 mmHg, a cuff slippage condition 1, indicated by the 4-point "V" in FIG. 2, has occurred.

As shown in FIG. 5B, slippage condition 2 occurs when each of five conditions occur. First, a slope of pressure samples during a cuff inflation must be greater than zero. Second, a pressure four samples previous to the current sample must be greater than the sum of a pressure reading three samples previous to the current sample and the product of 1.5 multiplied by the background noise. This condition is designated as P(n-4)>P(n-3)+1.5×noise. Third, a pressure at the current sample must be greater than the sum of a pressure one sample previous to the current sample and the product of 1.5 multiplied by the background noise. This condition is designated as P(n)>P(n-1)+1.5×noise. Fourth, a pressure two samples previous to the current sample must be less than a pressure three samples previous to the current sample. This condition is designated as P(n-2)<P(n-3). Fifth, a pressure two samples previous to the current sample must be less than a pressure one sample previous to the current sample. This condition is designated as P(n-2)<P(n-1). When all five of these conditions are met and when all samples used are greater than a minimum sample, typically 40 mmHg, a cuff slippage condition 2, indicated by the 5-point "V" in FIG. 3, has occurred.

As shown in FIG. 5C, slippage condition 3 occurs when each of three conditions occur. First, a slope of blood pressure readings during a cuff inflation must be greater than 0. Second, a blood pressure reading two samples previous to the current sample must be greater than the sum of a blood pressure reading one sample previous to the current sample and the product of 2.25 multiplied by the background noise. This condition is designated as P(n-2)>P(n-1)+2.25×noise. Third, a blood pressure reading one sample previous to the current sample must be greater than the sum of a blood pressure reading at the current sample and the product of 2.25 multiplied by the background noise. This condition is designated as P(n-1)>P(n)+2.25×noise. When all three of these conditions occur and all samples used are greater than a minimum sample, typically 40 mmHg, a cuff slippage condition 3 has occurred. Cuff slippage condition 3 indicates that a blood pressure drop of greater than the product of 2.25 multiplied by the background noise has occurred for two consecutive pressure samples during the current cuff inflation.

Figure 6:
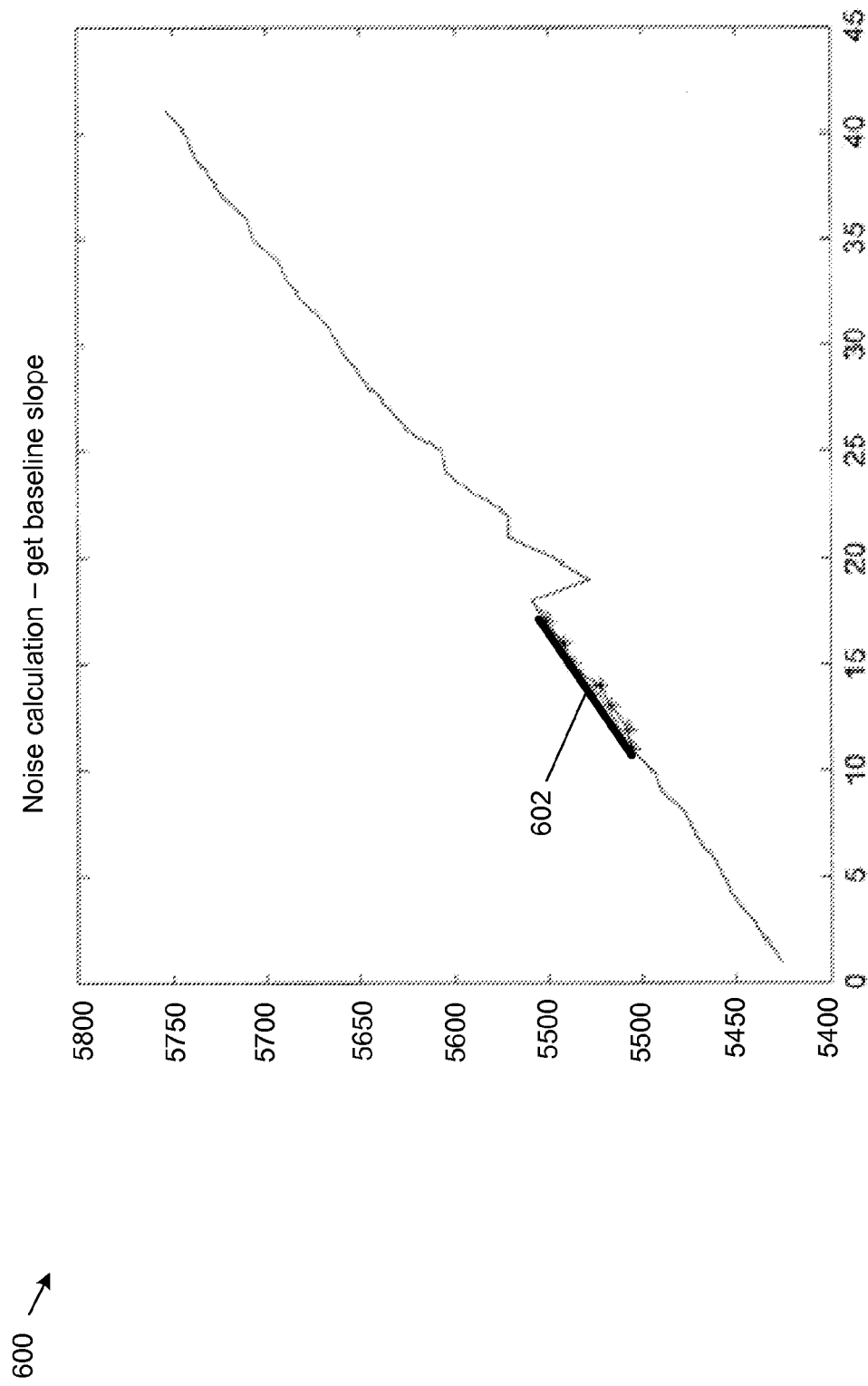
FIG. 6 shows an example pattern of pressure samples that illustrates an example background noise calculation for a cuff inflation.

FIG. 6 shows an example pattern of pressure samples 600 that illustrate an example background noise calculation for a cuff inflation. In this example, the background noise is derived from seven pressure samples during a cuff inflation. In other examples, more or less than seven samples may be used. Each of the samples occurs above a minimum level of pressure, typically 40 mmHg and each sample occurs when a slope of the pressure readings for the samples is greater than zero.

The first step in the background noise calculation is to determine a slope of a line 602 corresponding to the seven samples. In examples, the slope is equal to the highest pressure in the seven samples minus the lowest pressure in the seven samples divided by seven (the number of samples). This method of slope calculation is used throughout this disclosure. In other embodiments, other methods for calculating the slope may be used. For example, a method using least squares fit may be used.

Because the slope is positive, the highest pressure sample for the seven samples typically occurs for the last sample and the lowest pressure for the seven samples typically occurs for the first sample. In examples, because of variations along a positive slope, the highest and lowest pressures may occur for samples other than the last sample and the first sample.

Figure 7:
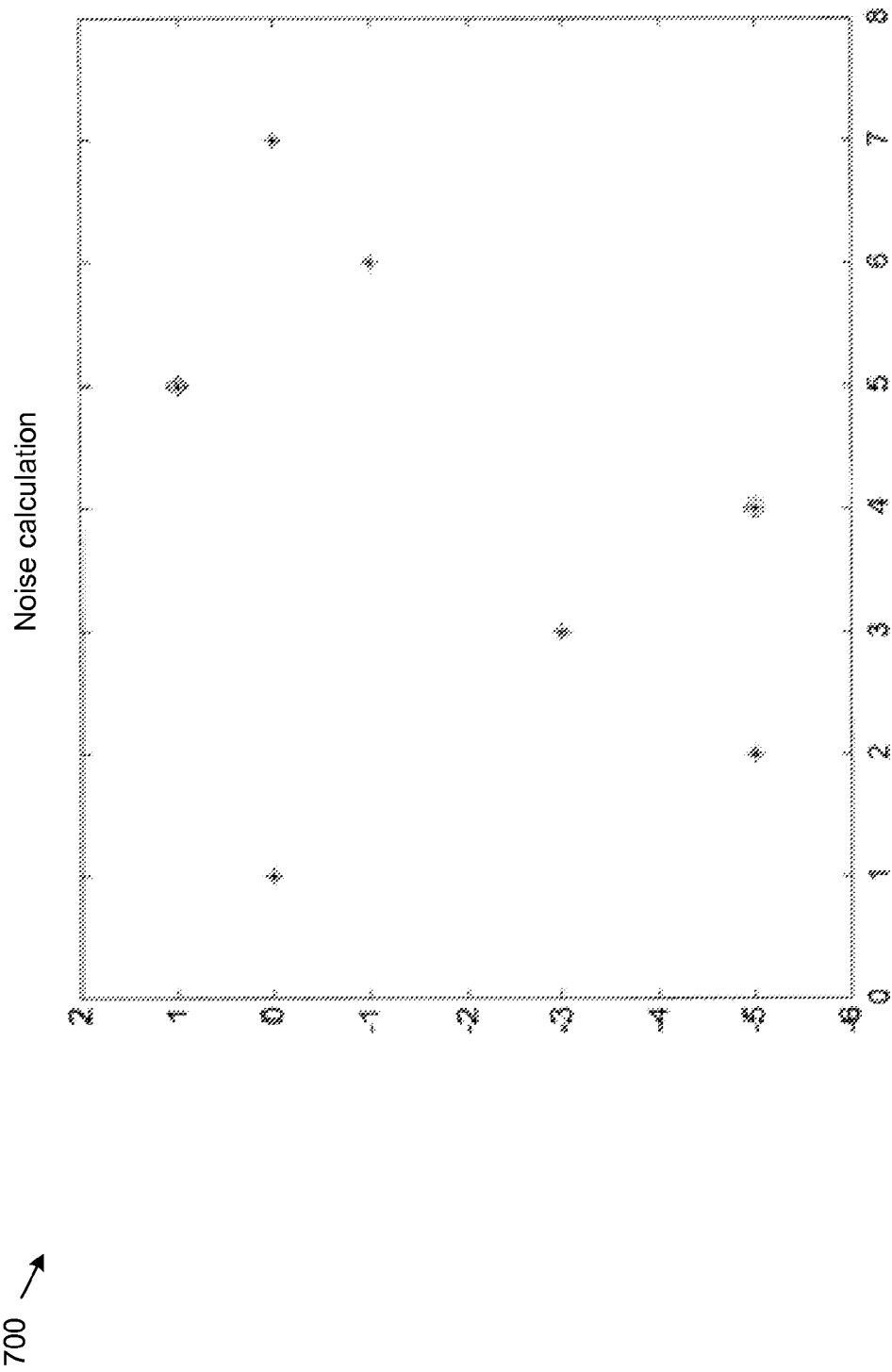
FIG. 7 shows an example of pressure deviations from an average used in a background noise calculation.

Once the slope is calculated, a determination is made as to a maximum deviation above and below the slope for the seven samples of pressure. As shown in FIG. 6, pressure samples for the samples, designated by an "x", are not all on the slope line. The background noise level is designated to be the difference between the maximum deviation above the slope and the maximum deviation below the slope. FIG. 7 is an example of seven samples showing deviations in pressure from an example slope line. The example shown in FIG. 7 does not correspond exactly to the pressure samples of FIG. 6, and is provided for illustration purposes only. As shown in FIG. 7, example samples 2 and 4 have maximum deviations of 5 below the slope line (represented by 0 on the vertical axis). Example sample 5 has a maximum deviation of 1 above the slope line. Therefore, for these seven samples, the background noise is equal to the difference in these maximum deviations or 6 (equal to 1 minus −5). For this example, a number of 6 is used for the noise in the equations used to calculate cuff slippage (as shown in FIGS. 5A-5C).

The background noise comes primarily from the operation of a pump used during the cuff inflation. In actual use, there may be slight differences in pump operation for each pump cycle that may cause pressure samples to be above or below the slope. Without reference to the background noise in the equations shown in FIGS. 5A, 5B and 5C, cuff slippage may be mistaken for background noise.

In examples, the background noise is calculated continually during the cuff inflation. As the cuff is inflated, pressure samples are obtained at a configured sampling rate, for example at a rate of 128 samples per second. When a plurality of pressure samples are obtained, the background noise is calculated and a determination is made as to whether a slippage condition has occurred. The number of samples in the plurality of samples comprises the number of samples used to calculate the background noise plus four additional samples. For the case where seven samples are used to calculate the background noise, the plurality of samples comprises a total of 11 samples.

After the background noise is calculated, a determination is made from the plurality of samples as to whether a slippage condition occurs. For example, if the plurality of samples comprises 11 samples, the background noise calculation is based on the first seven of these 11 samples. The first seven samples are the earliest of the 11 samples. The determination of a slippage condition is also based on a subset of these 11 samples, starting from the last sample, the last sample being P(n), one sample from the last being P(n-1), two samples from the last being P(n-2), etc. The last sample is the most recent of the 11 samples.

After the background noise is calculated and after a determination of whether a slippage condition occurs, a new pressure sample is obtained. For the example of seven samples being used for the background noise calculation plus four additional samples, this new pressure sample and the previous 10 pressure samples form a new plurality of 11 pressure samples that are used to recalculate the background noise and determine whether a slippage condition has occurred. After the background noise is recalculated from the first seven of this new plurality of samples, another determination of whether a slippage condition has occurred is made using this new plurality of 11 pressure samples. In a similar manner, for each succeeding pressure sample obtained during the cuff inflation, a new plurality of 11 pressure samples are used to recalculate the background noise and to determine whether a slippage condition has occurred.

Figure 8:
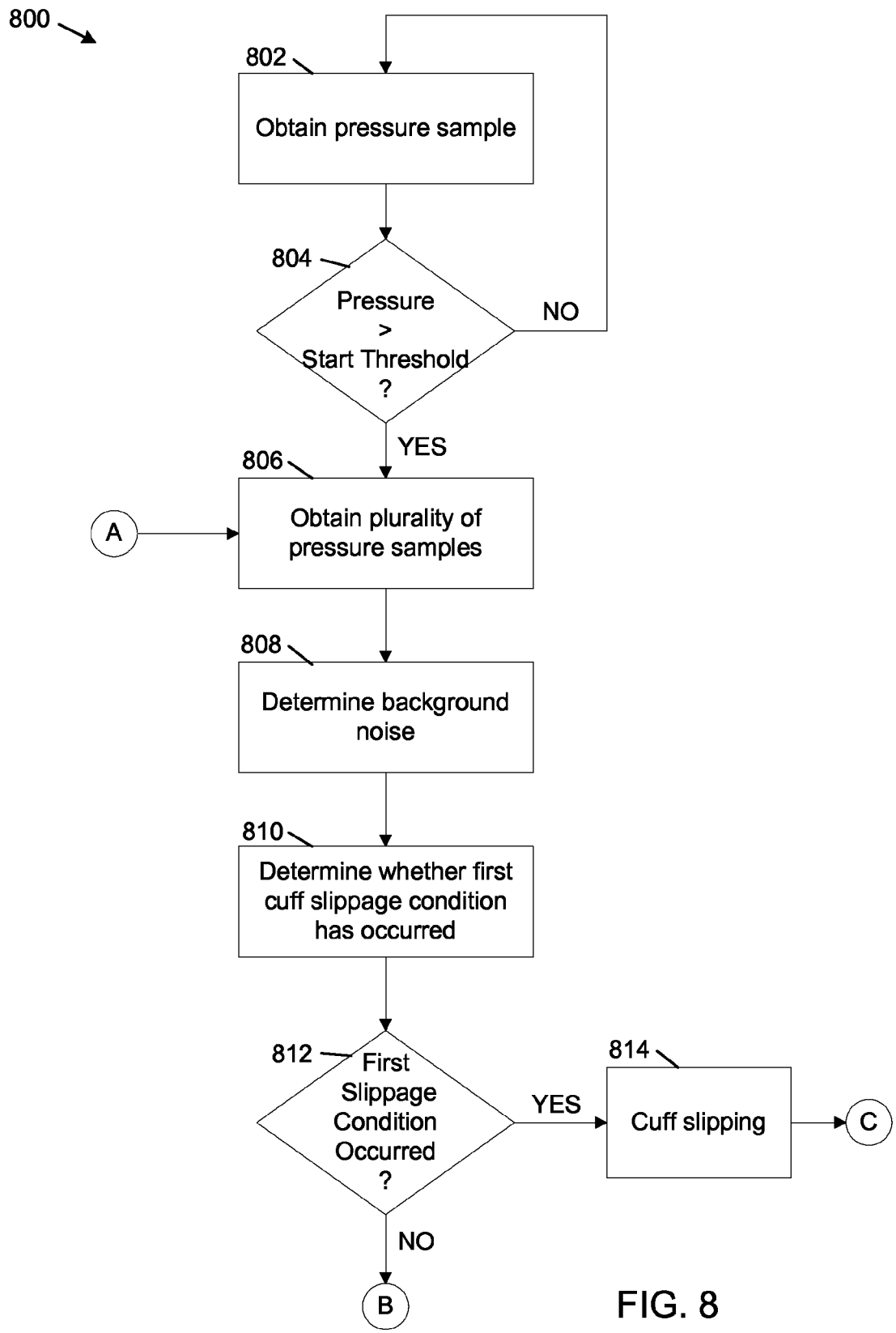
FIGS. 8, 9 and 10 show a flowchart of a method for determining cuff slippage during a blood pressure measurement on an automated blood pressure machine.
Figure 9:
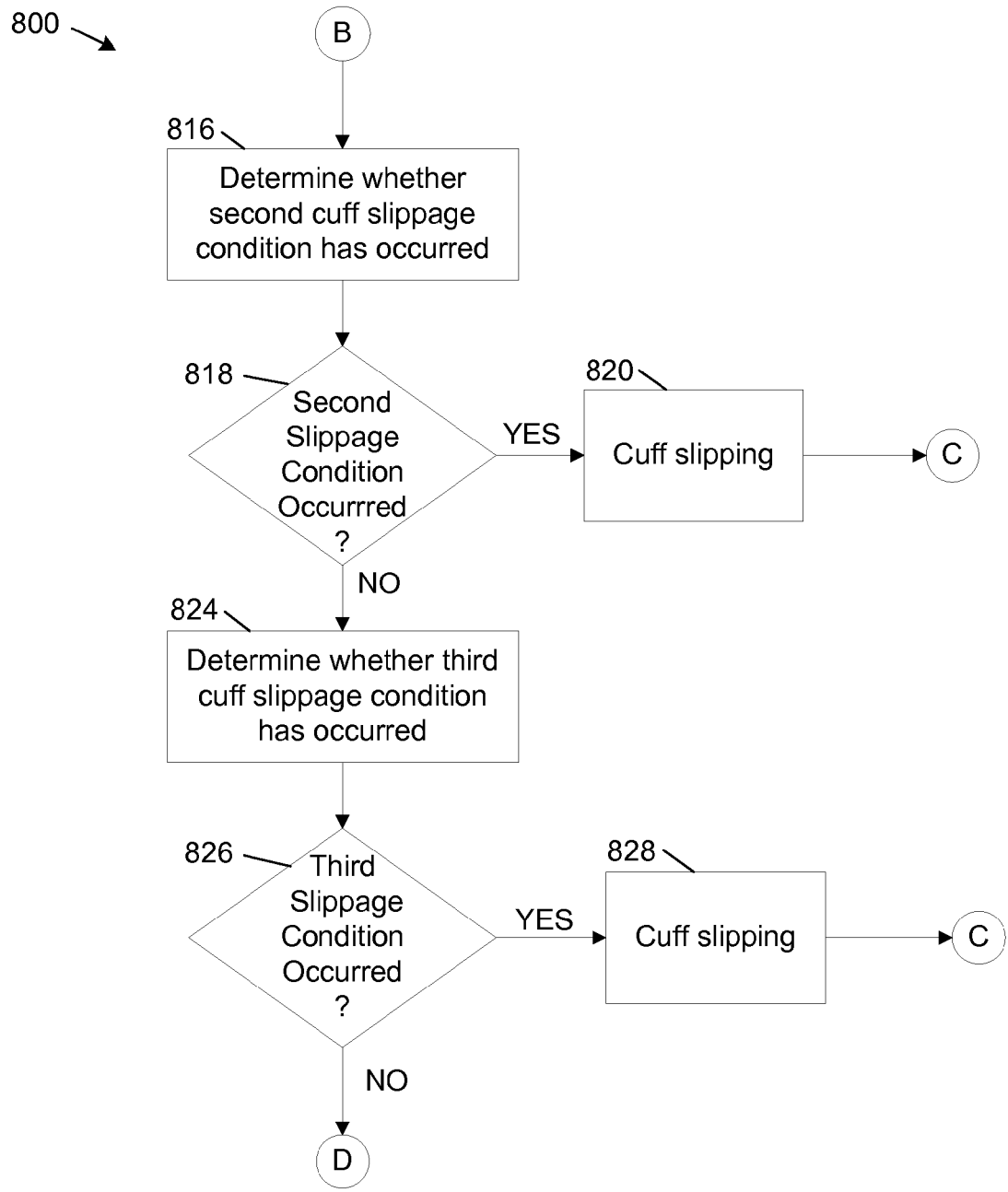
Figure 10:
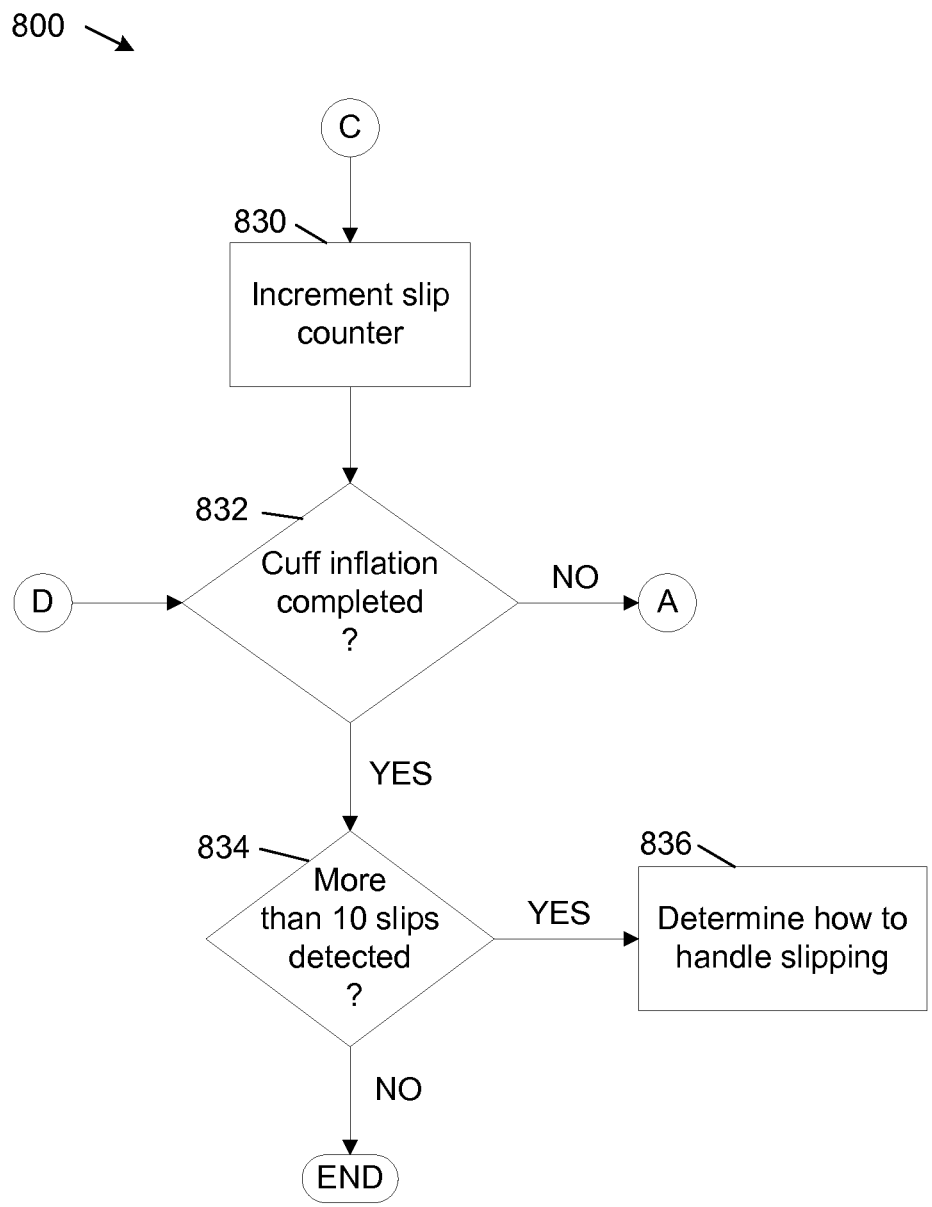

FIGS. 8, 9 and 10 show a flowchart illustrating an example method 800 for determining cuff slippage during a cuff inflation for a blood pressure measurement on an automated blood pressure machine. At operation 802 a pressure sample is taken. The pressure reading is one of many samples taken during the cuff inflation. An example sample rate is 128 pressure samples per second. In other examples more of fewer samples may be taken per second.

At operation 804, a determination is made was to whether the pressure for the current sample is higher than a minimum value, typically 40 mmHg. A minimum value is chosen because patients typically do not have blood pressures below the minimum value, so all samples below this value are ignored. When it is determined at operation 804 that the current pressure is below the minimum value, control returns to operation 802 and another pressure sample is taken.

When it is determined at operation 804 that the current blood pressure sample is above the minimum value, at operation 806, a plurality of pressure samples is obtained. The plurality of pressure samples includes a sample size of pressure samples needed to determine a background noise level. In examples, a sample size of seven is used. In other examples, more or fewer samples may be used. The plurality of pressure samples also includes four additional pressure samples used to determine whether a slippage condition has occurred. For the case where a sample size of seven is used to determine the background noise level, the plurality of pressure samples equals b 11 samples.

At operation 808, a background noise level is determined from the plurality of pressure samples. The background noise level is determined by calculating the slope of a line representing a slope for a subset of pressure samples in the plurality of pressure samples. In examples, the subset of pressure samples corresponds to the first seven pressure samples in the plurality of pressure samples. The slope is calculated by subtracting the lowest pressure in the subset from the highest pressure in the subset and dividing by the number of samples in the subset, in this case seven. Once the slope is determined, a maximum deviation of pressure above and below the slope is determined. The background noise represents the difference between the maximum deviation above the line and the maximum deviation below the line.

At operation 810, a determination is made as to whether a first cuff slippage condition has occurred. In examples, the first slippage condition corresponds to a 4-point "V" shape of blood pressure readings during the cuff inflation.

At operation 812, when a determination is made that the first cuff slippage condition has occurred, at operation 814, a designation is made that the blood pressure cuff has slipped. Control then passes to operation 830 where a slip counter is incremented. The slip counter is initially set at zero (not shown in FIG. 8). When the slip counter has a count of greater than 10, indicating that more than 10 slippages have been detected during the cuff inflation, a determination is made as to how to handle the slippage condition, as discussed later herein. The value of 10 is an arbitrary value. In other embodiments, a different value may be used.

At operation 812, when a determination is made that the first cuff slippage condition has not occurred, at operation 816, a determination is made as to whether a second cuff slippage condition has occurred. In examples, the second slippage condition corresponds to a 5-point "V" shape of pressure samples during the cuff inflation.

At operation 818, when a determination is made that the second cuff slippage condition has occurred, at operation 820, a designation is made that the blood pressure cuff has slipped. Control then passes to operation 830 where a slip counter is incremented. When the slip counter has a count of greater than 10, indicating that more than 10 slippages have been detected during the cuff inflation, a determination is made as to how to handle the slippage condition, as discussed later herein.

At operation 818, when a determination is made that the second cuff slippage condition has not occurred, at operation 824, a determination is made as to whether a third cuff slippage condition has occurred. In examples, the third slippage condition corresponds to two successive pressure drops greater than a pressure threshold during the cuff inflation. The pressure threshold for the third slippage condition is 2.25 multiplied by the background noise.

At operation 826, when it is determined that the third slippage condition has occurred, at operation 828, at operation 830 a slip counter is incremented. Control then advances to operation 832 where a determination is made as to whether cuff inflation has completed.

At operation 826, when is determined that the third slippage condition has not occurred, at operation 832 at determination is made as to whether the cuff inflation has completed.

When it is determined at operation 832 that the cuff inflation has not completed, control returns to operation 806 where a new plurality of pressure samples is obtained. For this new plurality of pressure samples, a background noise calculation is performed at operation 808 and then the pressure samples are evaluated to determine whether any of the first, second or third slippage conditions are detected.

When it is determined at operation 832 that cuff inflation has completed, at operation 834 a determination is made as to whether more than 10 slippage conditions have been detected during the cuff inflation. The slippage conditions may be any combination of the first slippage condition, the second slippage condition and the third slippage condition.

When it is determined at operation 834 that more than 10 slippage conditions have occurred during the cuff inflation, at operation 836 a determination is made as to how to handle slipping. In examples, the way in which slipping is handled is determined by whether a blood pressure reading is able to be calculated from the pressure samples obtained during the cuff inflation.

In examples, when the pressure samples are such that it is possible to calculate a blood pressure reading (comprising the calculation of a systolic blood pressure and a diastolic blood pressure), the blood pressure reading is displayed on the automated blood pressure machine. In addition, an operator is alerted that cuff slipping occurred during the cuff inflation. The alert may be an audible alert, a visual alert or a combination of both. However, in examples when the pressure samples are such that a blood pressure reading cannot be calculated, an error code is displayed on the automated blood pressure machine but a blood pressure reading is not provided.

Figure 11:
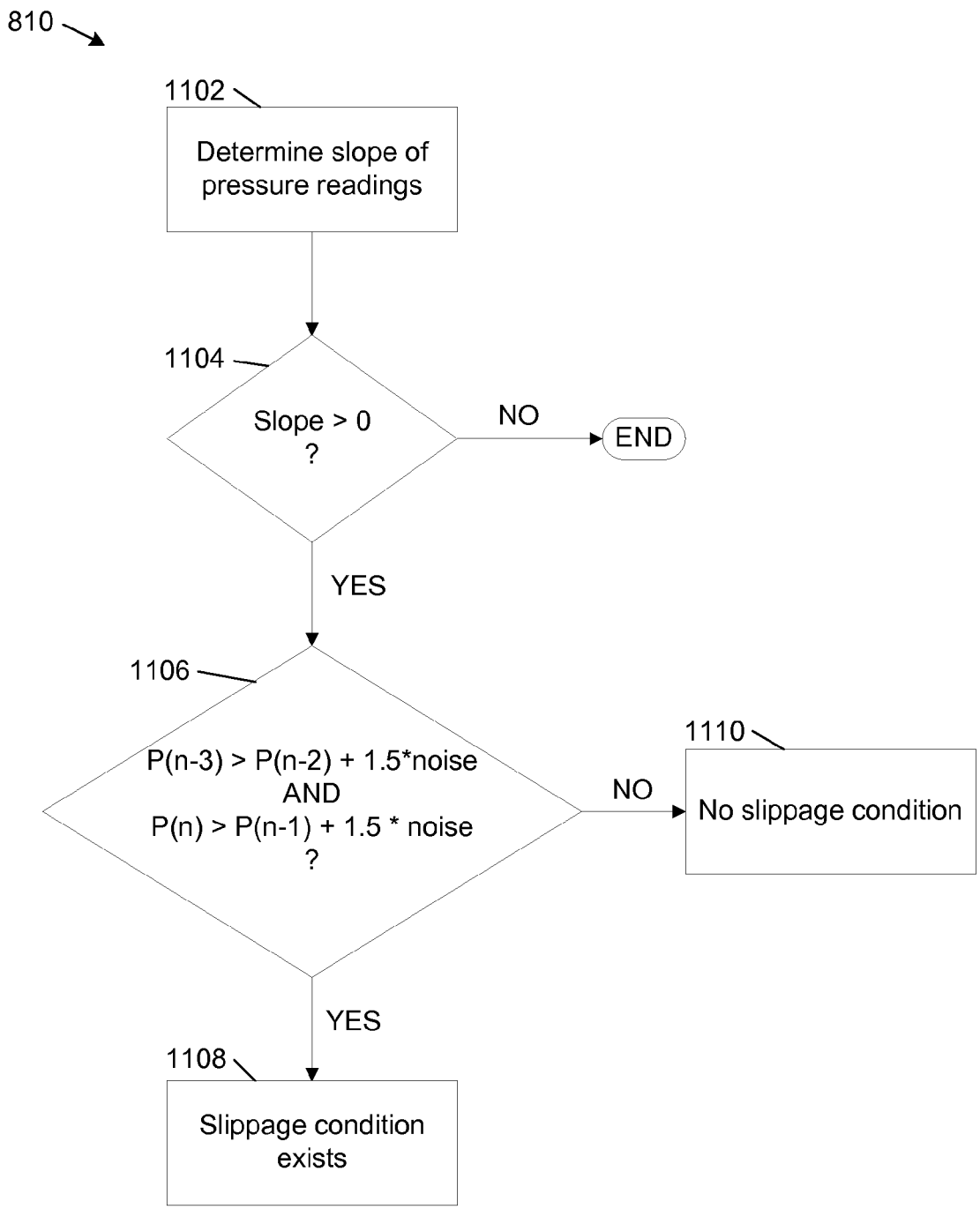
FIG. 11 shows a flow chart of a method for determining a first cuff slippage condition.

FIG. 11 shows a flow chart of a method 810 for determining whether the first slippage condition exists. In examples, the first slippage condition corresponds to a 4-point "V" shape of pressure samples during the cuff inflation.

At operation 1102, a slope of a line corresponding to the plurality of pressure samples from operation 806 is determined. The slope is calculated by determining a highest pressure sample and a lowest pressure sample from the first seven samples in the plurality of pressure samples, subtracting the lowest pressure sample from the highest pressure sample and dividing by the sample size, in this example dividing by seven.

At operation 1104, a determination is made as to whether the slope is greater than zero. When a determination is made that the slope is not greater than zero, the process to determine whether the first slippage condition occurs terminates.

At operation 1104, when a determination is made that the slope is greater than zero, at operation 1106, a determination is made whether a pressure three samples from the current sample is greater than the sum of a pressure two samples from the current sample and the product of 1.5 multiplied by the background noise and a determination is made whether a pressure at the current sample is greater than the sum of a pressure one sample from the current sample and the product of 1.5 multiplied by the background noise.

At operation 1106, when each of the above determinations is true, at operation 1108 a designation is made that the first slippage condition exists. At operation 1106, when at least one of the above determinations is false, at operation 1110 a designation is made that the first slippage condition does not exist.

Figure 12:
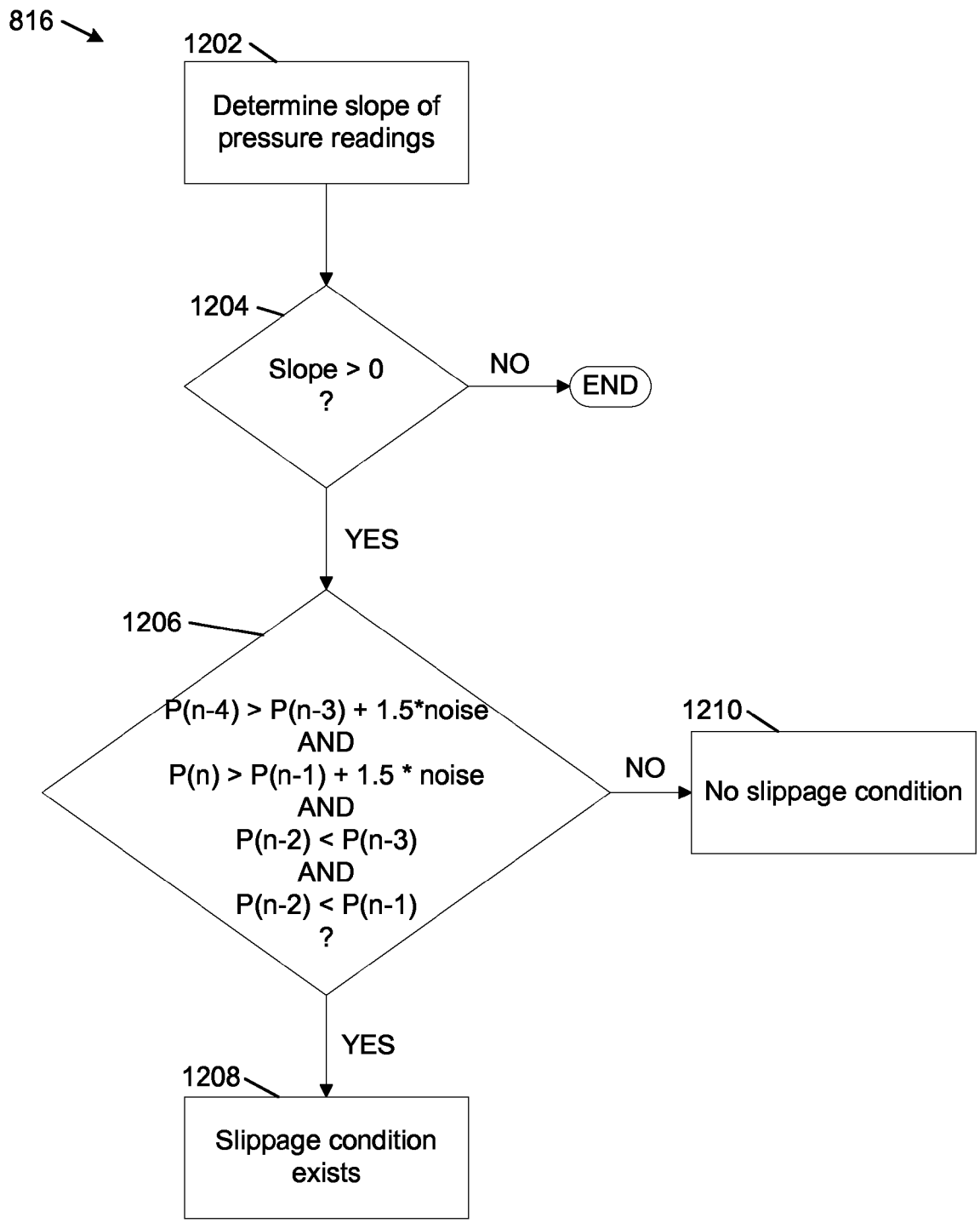
FIG. 12 shows a flow chart of a method for determining a second cuff slippage condition.

FIG. 12 shows a flow chart of a method 816 for determining whether the second slippage condition exists. In examples, the second slippage condition corresponds to a 5-point "V" shape of blood pressure readings during the cuff inflation.

At operation 1202, a slope of a line corresponding to the plurality of pressure samples from operation 806 is determined. The slope is calculated by determining a highest pressure sample and a lowest pressure sample from the first seven samples in the plurality of pressure samples, subtracting the lowest pressure sample from the highest pressure sample and dividing by the sample size, in this example dividing by seven.

At operation 1204, a determination is made as to whether the slope is greater than zero. When a determination is made that the slope is not greater than zero, the process to determine whether the second slippage condition occurs terminates.

At operation 1204, when a determination is made that the slope is greater than zero, at operation 1206, a determination is made whether a blood pressure reading four samples from the current sample is greater than the sum of a pressure sample three samples from the current sample and the product of 1.5 multiplied by the background noise, a determination is made whether a pressure sample at the current sample is greater than the sum of a pressure one sample from the current sample and the product of 1.5 multiplied by the background noise, a determination is made whether a pressure two samples from the current sample is less than a pressure three samples from the current sample and a determination is made whether a pressure two samples from the current sample is less than a pressure one sample from the current sample.

At operation 1206, when each of the above determinations is true, at operation 1208 a designation is made that the second slippage condition exists. At operation 1206, when at least one of the above determinations is false, at operation 1210 a designation is made that the second slippage condition does not exist.

Figure 13:
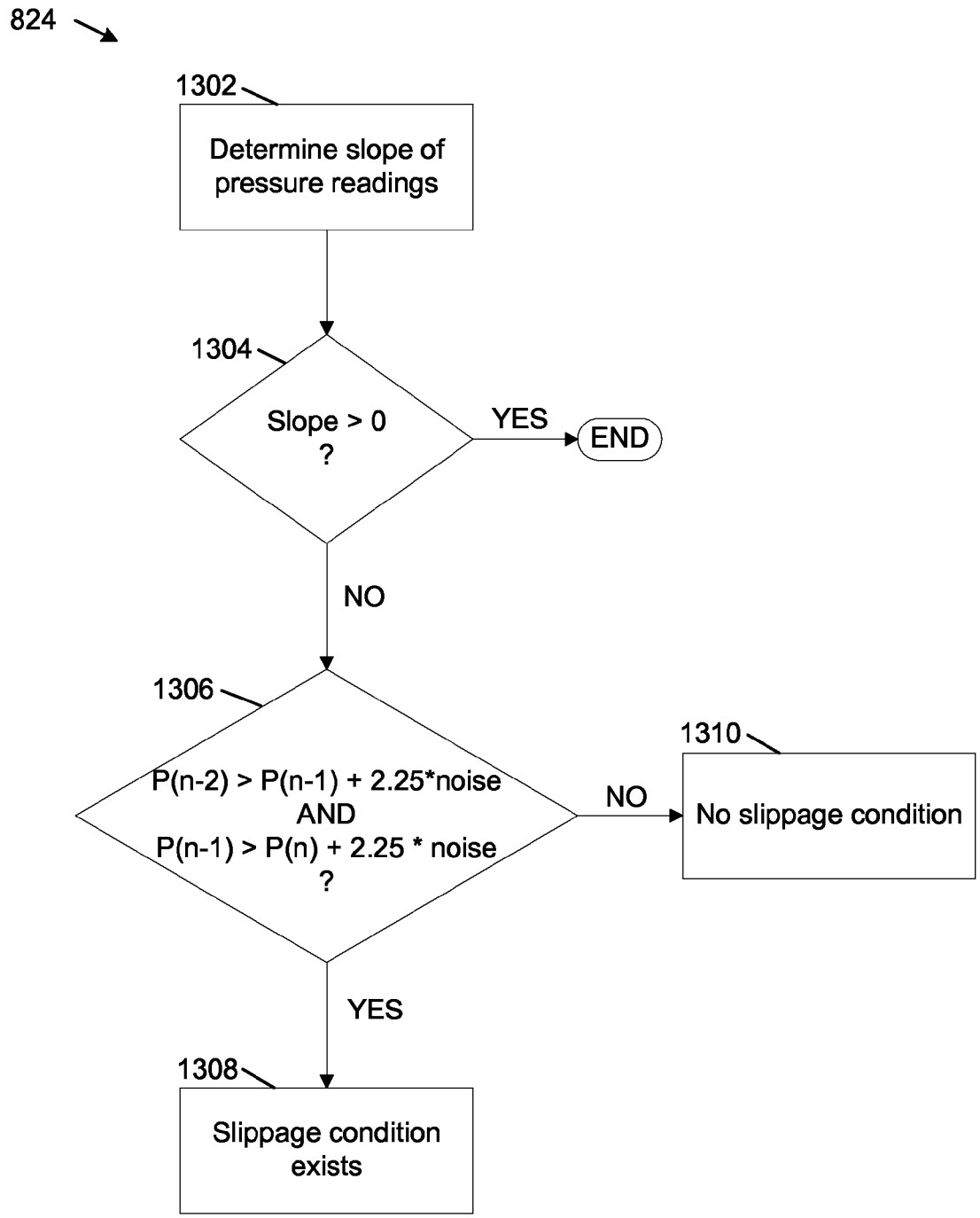
FIG. 13 shows a flow chart of a method for determining a third cuff slippage condition.

FIG. 13 shows a flow chart of a method 824 for determining whether the third slippage condition exists. In examples, the third slippage condition corresponds to a pressure drop of greater than 2.25 multiplied by the background noise for two successive pressure samples during a cuff inflation.

At operation 1302, a slope of a line corresponding to the plurality of pressure samples from operation 806 is determined. The slope is calculated by determining a highest pressure sample and a lowest pressure sample from the first seven samples in the plurality of pressure samples, subtracting the lowest pressure sample from the highest pressure sample and dividing by the sample size, in this example dividing by seven.

At operation 1304, a determination is made as to whether the slope is greater than zero. When a determination is made that the slope is not greater than zero, the process to determine whether the third slippage condition occurs terminates.

At operation 1304, when a determination is made that the slope is greater than zero, at operation 1306, a determination is made whether a pressure two samples from the current sample is greater than the sum of a pressure one sample from the current sample and the product of 2.25 multiplied by the background noise level and a determination is made whether a pressure one sample from the current sample is greater than the sum of a blood pressure reading from the current sample and the product of 2.25 multiplied by the background noise.

At operation 1306, when each of the above determinations is true, at operation 1308 a designation is made that the second slippage condition exists. At operation 1306, when at least one of the above determinations is false, at operation 1310 a designation is made that the second slippage condition does not exist.

Figure 14:
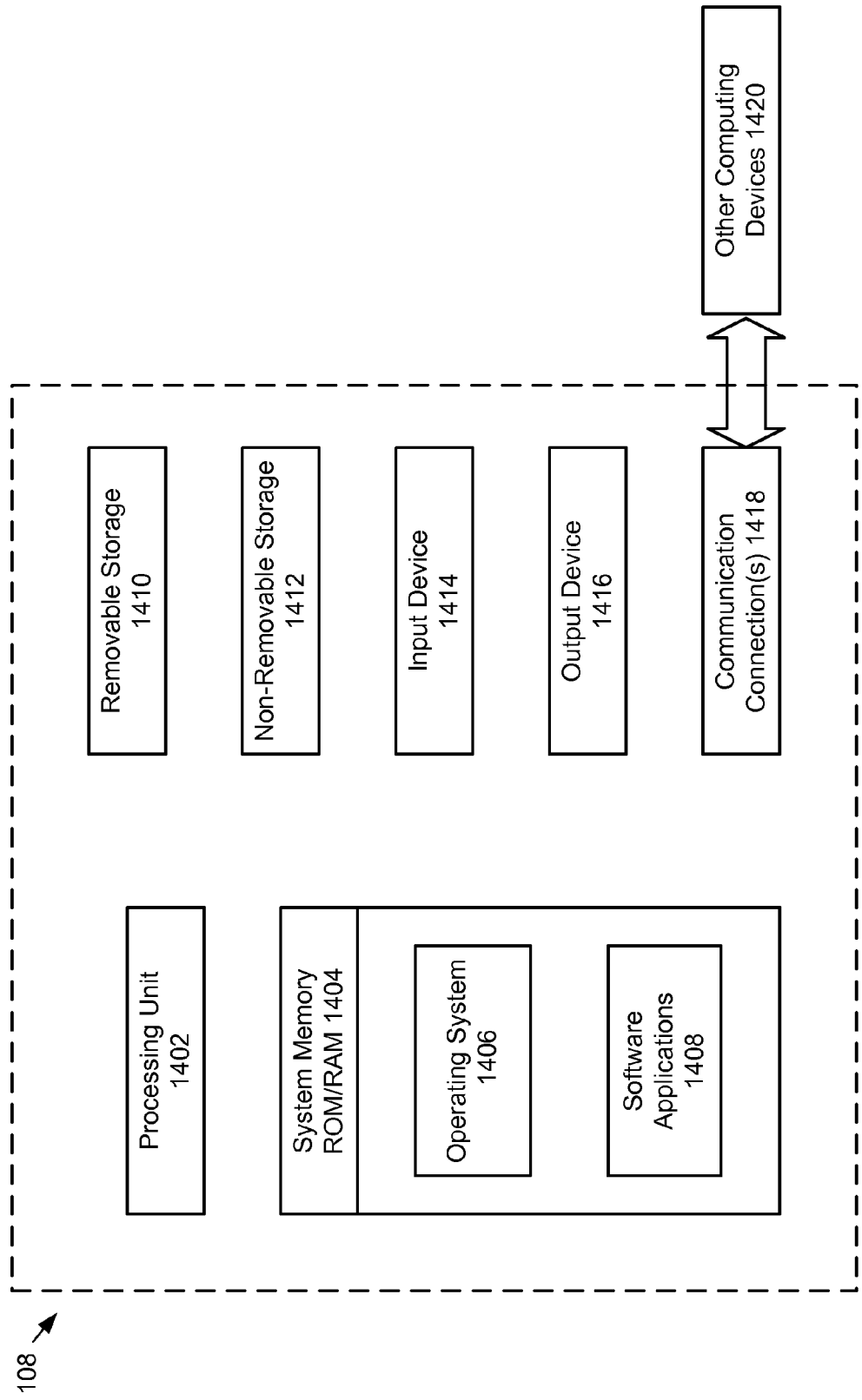
FIG. 14 shows example components of the automatic blood pressure machine of FIG. 1.

With reference to FIG. 14, example components of an automatic blood pressure machine 108 are shown. The automatic blood pressure machine 108 can include input/output devices, a central processing unit ("CPU"), a data storage device, and a network device.

In a basic configuration, the automatic blood pressure machine 108 typically includes at least one processing unit 1402 and system memory 1404. Depending on the exact configuration and type of computing device, the system memory 1404 may be volatile (such as RAM), non-volatile (such as ROM, flash memory, etc.) or some combination of the two. System memory 1404 typically includes an operating system 1406 suitable for controlling the operation of an automatic blood pressure machine. The system memory 1404 may also include one or more software applications 1408 and may include program data.

The automatic blood pressure machine 108 may have additional features or functionality. For example, the automatic blood pressure machine 108 may also include computer readable media. Computer readable media can include both computer readable storage media and communication media.

Computer readable storage media is physical media, such as data storage devices (removable and/or non-removable) including magnetic disks, optical disks, or tape. Such additional storage is illustrated in FIG. 14 by removable storage 1410 and non-removable storage 1412. Computer readable storage media may include volatile and nonvolatile, removable and non-removable media implemented in any method or technology for storage of information, such as computer readable instructions, data structures, program modules, or other data. Computer readable storage media can include, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by automatic blood pressure machine 108. Any such computer readable storage media may be part of the automatic blood pressure machine 108.

The automatic blood pressure machine 108 may also contain communication connections 1418 that allow the device to communicate with other computing devices 1420, such as over a network in a distributed computing environment, for example, an intranet or the Internet. Communication connections 1418 are one example of communication media. Communication media may typically be embodied by computer readable instructions, data structures, program modules, or other data in a modulated data signal, such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media.

The various embodiments described above are provided by way of illustration only and should not be construed to limiting. Various modifications and changes that may be made to the embodiments described above without departing from the true spirit and scope of the disclosure.

What is claimed is:

1. A method for determining cuff slippage in a blood pressure monitoring device, the method comprising:
   on the blood pressure monitoring device, starting a cuff inflation including inflating a blood pressure cuff;
   obtaining a plurality of pressure samples when the blood pressure cuff is inflating;
   determining, by a processing device, whether a slope corresponding to the plurality of pressure samples is a positive number;
   when it is determined that the slope is a positive number, determining the processing device, a level of background noise during the blood pressure cuff inflation, the level of background noise being determined from the plurality of pressure samples; and
   when the background noise is determined, determining, by the processing device, from the plurality of pressure samples whether a pressure pattern indicating cuff slippage is obtained;
   wherein determining from the plurality of pressure samples whether a pressure sample pattern indicating cuff slippage is obtained comprises:
      obtaining the last pressure sample in the plurality of pressure samples;
      obtaining the first from last pressure sample in the plurality of pressure samples;
      obtaining the second from last pressure sample in the plurality of pressure samples;
      obtaining the third from last pressure sample in the plurality of pressure samples;
      determining whether the third from last pressure sample is greater than the sum of the second from the last pressure sample and the product of 1.5 multiplied by the level of background noise;
      determining whether the last pressure sample is greater than the sum of the first from last pressure sample and the product of 1.5 multiplied by the level of background noise; and
      when it is determined that the third from last pressure sample is greater than the sum of the second from last pressure sample and the product of 1.5 multiplied by the level of background noise and when it is determined that the last pressure sample is greater than the sum of the first from last pressure sample and the product of 1.5 multiplied by the level of background noise, making a determination that a cuff slippage condition exists.

2. The method of claim 1, wherein determining whether the slope corresponding to the plurality of pressure samples is a positive number comprises:
   obtaining a subset of the plurality of pressure samples;
   obtaining a first pressure sample from the subset of the plurality of pressure samples, the first pressure sample being a lowest pressure in the subset of the plurality of pressure samples;
   obtaining a second pressure sample from subset of the plurality of pressure samples, the second pressure sample being a highest pressure in the subset of the plurality of pressure samples;
   calculating the slope, the calculation of the slope comprising:
      subtracting the first pressure sample from the second pressure sample;
      dividing a result of the subtraction of the first pressure sample from the second pressure sample by the number of pressure samples in the subset of the plurality of pressure samples; and
   when the slope is greater than zero, making a determination that the slope is a positive number.

3. The method of claim 1, wherein determining the level of background noise during the cuff inflation comprises:
   obtaining a subset of the plurality of pressure samples;
   obtaining a first pressure sample from the subset of the plurality of pressure samples, the first pressure sample being a lowest pressure in the subset of the plurality of pressure samples;
   obtaining a second pressure sample from subset of the plurality of pressure samples, the second pressure sample being a highest pressure in the subset of the plurality of pressure samples;
   calculating a slope, the calculation of the slope comprising:
      subtracting the first pressure sample from the second pressure sample; and
      dividing a result of the subtraction of the first pressure sample from the second pressure sample by the number of pressure samples in the subset of the plurality of pressure samples;
   determining a maximum pressure sample above the calculated slope;
   determining a maximum pressure sample below the calculated slope; and
   subtracting the maximum pressure sample below the calculated slope from the maximum pressure sample above the calculated slope, the result of the subtraction being designated as the level of background noise.

4. The method of claim 3, wherein the number of pressure samples in the subset of the plurality of pressure samples is seven.

5. The method of claim 1, wherein the plurality of pressure samples is obtained after a minimum pressure is reached.

6. An electronic computing system comprising:
   a processing unit; and
   a data storage system, the data storage system storing instructions that, when executed by the processing unit, cause the electronic computing system to:
      start a cuff inflation, the cuff inflation comprising inflating the blood pressure cuff and obtaining a plurality of pressure samples when the blood pressure cuff is inflating;
      determine whether a slope corresponding to the plurality of pressure samples is a positive number;
      when it is determined that the slope is a positive number, determine a level of background noise during the cuff inflation, the level of background noise being determined from the plurality of pressure samples; and
      when the background noise is determined, determine from the plurality of pressure samples whether a pressure pattern indicating cuff slippage is obtained, including:
  obtaining the last pressure sample in the plurality of pressure samples;
  obtaining the first from last pressure sample in the plurality of pressure samples;
  obtaining the second from last pressure sample in the plurality of pressure samples;
  obtaining the third from last pressure sample in the plurality of pressure samples;
  determining whether the third from the last pressure sample is greater than the sum of the second from the last pressure sample and the product of 1.5 multiplied by the level of background noise;
  determining whether the last pressure sample is greater than the sum of the first from the last pressure sample and the product of 1.5 multiplied by the level of background noise; and
  when it is determined that the third from the last pressure sample is greater than the sum of the second from the last pressure sample and the product of 1.5 multiplied by the level of background noise and when it is determined that the last pressure sample is greater than the sum of the first from last pressure sample and the product of 1.5 multiplied by the level of background noise, making a determination that a cuff slippage condition exists.

7. The electronic computing system of claim 6, wherein determining whether the slope corresponding to the plurality of pressure samples is a positive number comprises:
  obtaining a subset of the plurality of pressure samples;
  obtaining a first pressure sample from the subset of the plurality of pressure samples, the first pressure sample being a lowest pressure in the subset of the plurality of pressure samples;
  obtaining a second pressure sample from subset of the plurality of pressure samples, the second pressure sample being a highest pressure in the subset of the plurality of pressure samples;
  calculating the slope, the calculation of the slope comprising:
    subtracting the first pressure sample from the second pressure sample; and
    dividing a result of the subtraction of the first pressure sample from the second pressure sample by the number of pressure samples in the subset of the plurality of pressure samples; and
  when the slope is greater than zero, making a determination that the slope is a positive number.

8. The electronic computing system of claim 6, wherein determining the level of background noise during the cuff inflation comprises:
  obtaining a subset of the plurality of pressure samples;
  obtaining a first pressure sample from the subset of the plurality of pressure samples, the first pressure sample being a lowest pressure in the subset of the plurality of pressure samples;
  obtaining a second pressure sample from subset of the plurality of pressure samples, the second pressure sample being a highest pressure in the subset of the plurality of pressure samples;
  calculating a slope, the calculation of the slope comprising:
    subtracting the first pressure sample from the second pressure sample; and
    dividing a result of the subtraction of the first pressure sample from the second pressure sample by the number of pressure samples in the subset of the plurality of pressure samples;
  determining a maximum pressure sample below the calculated slope; and
  subtracting the maximum pressure sample below the calculated slope from the maximum pressure sample above the calculated slope, the result of the subtraction being designated as the level of background noise.

9. The electronic computing system of claim 6, wherein when more than 10 slippage conditions occur, taking a form of action, the form of action comprising initiating a cuff deflation cycle and setting an alert for a user to alert the user to the slippage condition.

10. A method for determining cuff slippage in a blood pressure monitoring device, the method comprising:
  on the blood pressure monitoring device, starting a cuff inflation including inflating a blood pressure cuff;
  obtaining a plurality of pressure samples when the blood pressure cuff is inflating;
  determining, by a processing device, whether a slope corresponding to the plurality of pressure samples is a positive number;
  when it is determined that the slope is a positive number, determining, by the processing device, a level of background noise during the blood pressure cuff inflation, the level of background noise being determined from the plurality of pressure samples; and
  when the background noise is determined, determining, by the processing device, from the plurality of pressure samples whether a pressure pattern indicating cuff slippage is obtained;
  wherein determining from the plurality of pressure samples whether a pressure sample pattern indicating cuff slippage is obtained comprises:
    obtaining the last pressure sample in the plurality of pressure samples;
    obtaining the first from last pressure sample in the plurality of pressure samples;
    obtaining the second from last pressure sample in the plurality of pressure samples;
    obtaining the third from last pressure sample in the plurality of pressure samples;
    obtaining the fourth from last pressure sample in the plurality of pressure samples;
    determining whether the fourth from the last pressure sample is greater than the sum of the third from the last pressure sample and the product of 1.5 multiplied by the level of background noise;
    determining whether the last pressure sample is greater than the sum of the first from the last pressure sample and the product of 1.5 multiplied by the level of background noise;
    determining whether the second from the last pressure sample is less than the third from the last pressure sample;
    determining whether the second from the last pressure sample is less than the first from the last pressure sample; and
    when it is determined that the fourth from the last pressure sample is greater than the sum of the third from the last pressure sample and the product of 1.5 multiplied by the level of background noise and when it is determined that the last pressure sample is greater than the sum of the first from last pressure sample and the product of 1.5 multiplied by the level of background noise and when it is determined that the second from the last pressure sample is less than the third from the last pressure sample and when it is determined that the second from the last pressure sample is less than the first from the last pressure sample, making a determination that a cuff slippage condition exists.

11. An electronic computing system comprising:

a processing unit; and a data storage system, the data storage system storing instructions that, when executed by the processing unit, cause the electronic computing system to:

start a cuff inflation, the cuff inflation comprising inflating the blood pressure cuff and obtaining a plurality of pressure samples when the blood pressure cuff is inflating;

determine whether a slope corresponding to the plurality of pressure samples is a positive number;

when it is determined that the slope is a positive number, determine a level of background noise during the cuff inflation, the level of background noise being determined from the plurality of pressure samples; and when the background noise is determined, determine from the plurality of pressure samples whether a pressure pattern indicating cuff slippage is obtained, including:

obtaining the last pressure sample in the plurality of pressure samples;

obtaining the first from last pressure sample in the plurality of pressure samples;

obtaining the second from last pressure sample in the plurality of pressure samples;

obtaining the third from last pressure sample in the plurality of pressure samples; obtaining the fourth from last pressure sample in the plurality of pressure samples;

determining whether the fourth from the last pressure sample is greater than the sum of the third from the last pressure sample and the product of 1.5 multiplied by the level of background noise;

determining whether the last pressure sample is greater than the sum of the first from the last pressure sample and the product of 1.5 multiplied by the level of background noise;

determining whether the second from the last pressure sample is less than the third from the last pressure sample;

determining whether the second from the last pressure sample is less than the first from the last pressure sample;

when it is determined that the fourth from the last pressure sample is greater than the sum of the third from the last pressure sample and the product of 1.5 multiplied by the level of background noise and when it is determined that the last pressure sample is greater than the sum of the first from last pressure sample and the product of 1.5 multiplied by the level of background noise and when it is determined that the second from the last pressure sample is less than the third from the last pressure sample and when it is determined that the second from the last pressure sample is less than the first from the last pressure sample, making a determination that a cuff slippage condition exists.

\* \* \* \* \*